(12) United States Patent
Salas

(10) Patent No.: US 8,945,151 B2
(45) Date of Patent: Feb. 3, 2015

(54) SURGICAL CLIP APPLICATOR AND APPARATUS INCLUDING THE SAME

(75) Inventor: Allan Salas, Pleasanton, CA (US)

(73) Assignee: AtriCure, Inc., West Chester, OH (US)

( * ) Notice: Subject to any disclaimer, the term of this patent is extended or adjusted under 35 U.S.C. 154(b) by 1073 days.

(21) Appl. No.: 11/180,820

(22) Filed: Jul. 13, 2005

(65) Prior Publication Data

US 2007/0016228 A1    Jan. 18, 2007

(51) Int. Cl.
*A61B 17/10* (2006.01)
*A61B 17/122* (2006.01)
*A61B 17/128* (2006.01)
*A61B 17/28* (2006.01)

(52) U.S. Cl.
CPC ............. *A61B 17/122* (2013.01); *A61B 17/128* (2013.01); *A61B 2017/2825* (2013.01)
USPC ............ 606/139; 606/157; 606/158; 606/207

(58) Field of Classification Search
CPC .... A61B 17/12; A61B 17/122; A61B 17/128; A61B 2017/2825
USPC .................. 606/1.6, 142, 148, 151, 207, 139, 606/157–158, 205, 219; 227/175.1
See application file for complete search history.

(56) References Cited

U.S. PATENT DOCUMENTS

| | | | |
|---|---|---|---|
| 2,743,726 A | 5/1956 | Grieshaber | |
| 2,890,519 A * | 6/1959 | Storz, Jr. ......................... | 29/225 |
| 3,154,281 A | 10/1964 | Frank | |
| 3,174,309 A | 3/1965 | Kobayashi | |
| 3,503,398 A * | 3/1970 | Raible et. al. ................. | 606/207 |
| 4,201,213 A | 5/1980 | Townsend | |
| 4,616,651 A * | 10/1986 | Golden .......................... | 606/142 |
| 4,819,633 A | 4/1989 | Bauer et al. | |
| 4,821,719 A | 4/1989 | Fogarty | |

(Continued)

FOREIGN PATENT DOCUMENTS

| | | |
|---|---|---|
| EP | 0106748 A1 | 4/1984 |
| EP | 0856291 A2 | 8/1998 |

(Continued)

OTHER PUBLICATIONS

Office Action dated Mar. 4, 2003, for U.S. Appl. No. 10/080,374, filed Feb. 19, 2002, Inventor: David K. Swanson (14 pages).

(Continued)

*Primary Examiner* — Mark Mashack
(74) *Attorney, Agent, or Firm* — Kilpatrick Townsend & Stockton LLP

(57) ABSTRACT

Apparatus and methods for delivering a surgical clip to a patient during a minimally invasive surgical procedure are disclosed herein. An exemplary apparatus for isolating an atrial appendage of a patient includes a surgical clip that locks onto the atrial appendage of the patient, and a surgical clip applicator that releasably engages the surgical clip. The surgical clip can include a top portion and a bottom portion. The surgical clip applicator can include a first flexible flap and a second flexible flap. The first and second flexible flaps can be sufficiently rigid to prevent the surgical clip from falling off of the surgical clip applicator when the surgical clip is engaged to the surgical applicator and the surgical clip applicator is in a relaxed state, and sufficiently flexible to facilitate separation of the surgical clip from the surgical clip applicator when the surgical clip is locked onto the atrial appendage.

11 Claims, 5 Drawing Sheets

(56) References Cited

U.S. PATENT DOCUMENTS

| | | | |
|---|---|---|---|
| 4,834,090 A | 5/1989 | Moore | |
| 4,950,258 A * | 8/1990 | Kawai et al. | 604/530 |
| 4,985,030 A | 1/1991 | Melzer et al. | |
| 5,151,102 A | 9/1992 | Kamiyama et al. | |
| 5,190,541 A | 3/1993 | Abele et al. | |
| 5,250,072 A | 10/1993 | Jain | |
| 5,300,087 A | 4/1994 | Knoepfler | |
| 5,398,683 A | 3/1995 | Edwards et al. | |
| 5,441,483 A | 8/1995 | Avitall | |
| 5,450,846 A | 9/1995 | Goldreyer | |
| 5,484,435 A | 1/1996 | Fleenor et al. | |
| 5,497,933 A * | 3/1996 | DeFonzo et al. | 227/175.1 |
| 5,545,193 A | 8/1996 | Fleischman et al. | |
| 5,546,682 A | 8/1996 | Skerry | |
| 5,569,274 A | 10/1996 | Rapacki et al. | |
| 5,582,609 A | 12/1996 | Swanson et al. | |
| 5,599,350 A | 2/1997 | Schulze et al. | |
| 5,637,090 A | 6/1997 | McGee et al. | |
| 5,755,715 A | 5/1998 | Stern et al. | |
| 5,776,130 A | 7/1998 | Buysse et al. | |
| 5,782,899 A | 7/1998 | Imran | |
| 5,797,905 A | 8/1998 | Fleischman et al. | |
| 5,820,095 A | 10/1998 | Stone | |
| 5,824,005 A | 10/1998 | Motamedi et al. | |
| 5,846,239 A | 12/1998 | Swanson et al. | |
| 5,868,362 A | 2/1999 | Daoud | |
| 5,888,198 A | 3/1999 | Eggers et al. | |
| 5,891,095 A | 4/1999 | Eggers et al. | |
| 5,921,990 A * | 7/1999 | Webb | 606/110 |
| 5,925,038 A | 7/1999 | Panescu et al. | |
| 5,938,694 A | 8/1999 | Jaraczewski et al. | |
| 5,961,513 A | 10/1999 | Swanson et al. | |
| 5,971,983 A | 10/1999 | Lesh | |
| 6,004,269 A | 12/1999 | Crowley et al. | |
| 6,010,500 A | 1/2000 | Sherman et al. | |
| 6,010,516 A | 1/2000 | Hulka | |
| 6,023,638 A | 2/2000 | Swanson | |
| 6,039,748 A | 3/2000 | Savage et al. | |
| 6,096,033 A | 8/2000 | Tu et al. | |
| 6,096,037 A | 8/2000 | Mulier et al. | |
| 6,115,626 A | 9/2000 | Whayne et al. | |
| 6,142,994 A | 11/2000 | Swanson et al. | |
| 6,162,220 A | 12/2000 | Nezhat | |
| 6,174,309 B1 | 1/2001 | Wrublewski et al. | |
| 6,245,068 B1 | 6/2001 | Olson et al. | |
| 6,267,761 B1 | 7/2001 | Ryan | |
| 6,273,887 B1 | 8/2001 | Yamauchi et al. | |
| 6,277,117 B1 | 8/2001 | Tetzlaff et al. | |
| 6,296,640 B1 | 10/2001 | Wampler et al. | |
| 6,312,425 B1 | 11/2001 | Simpson et al. | |
| 6,325,797 B1 | 12/2001 | Stewart et al. | |
| 6,330,473 B1 | 12/2001 | Swanson et al. | |
| 6,334,861 B1 | 1/2002 | Chandler et al. | |
| 6,395,325 B1 | 5/2002 | Hedge et al. | |
| 6,416,508 B1 | 7/2002 | Eggers et al. | |
| 6,432,103 B1 | 8/2002 | Ellsberry et al. | |
| 6,454,766 B1 | 9/2002 | Swanson et al. | |
| 6,464,700 B1 | 10/2002 | Koblish et al. | |
| 6,471,699 B1 | 10/2002 | Fleischman et al. | |
| 6,511,480 B1 | 1/2003 | Tetzlaff et al. | |
| 6,517,536 B2 | 2/2003 | Hooven et al. | |
| 6,529,756 B1 | 3/2003 | Phan et al. | |
| 6,533,784 B2 | 3/2003 | Truckai et al. | |
| 6,542,781 B1 | 4/2003 | Koblish et al. | |
| 6,544,262 B2 | 4/2003 | Fleischman | |
| 6,558,408 B1 | 5/2003 | Fogarty et al. | |
| 6,582,429 B2 | 6/2003 | Krishnan et al. | |
| 6,584,360 B2 | 6/2003 | Francischelli et al. | |
| 6,595,991 B2 | 7/2003 | Tollner et al. | |
| 6,610,055 B1 | 8/2003 | Swanson et al. | |
| 6,645,202 B1 | 11/2003 | Pless et al. | |
| 6,663,622 B1 | 12/2003 | Foley et al. | |
| 6,679,882 B1 | 1/2004 | Kornerup | |
| 6,685,715 B2 | 2/2004 | Danitz et al. | |
| 6,692,491 B1 | 2/2004 | Phan | |
| 6,692,514 B2 | 2/2004 | Fogarty et al. | |
| 6,706,038 B2 | 3/2004 | Francischelli et al. | |
| 6,771,996 B2 | 8/2004 | Bowe et al. | |
| 6,786,905 B2 | 9/2004 | Swanson et al. | |
| 6,807,968 B2 | 10/2004 | Francischelli et al. | |
| 6,837,887 B2 | 1/2005 | Woloszko et al. | |
| 6,896,673 B2 | 5/2005 | Hooven | |
| 6,899,710 B2 | 5/2005 | Hooven | |
| 6,926,712 B2 * | 8/2005 | Phan | 606/41 |
| 6,932,816 B2 | 8/2005 | Phan | |
| 6,939,350 B2 | 9/2005 | Phan | |
| 6,949,098 B2 | 9/2005 | Mulier et al. | |
| 6,997,925 B2 | 2/2006 | Maguire et al. | |
| 7,150,097 B2 | 12/2006 | Sremcich et al. | |
| 2002/0002372 A1 | 1/2002 | Jahns et al. | |
| 2002/0177859 A1 * | 11/2002 | Monassevitch et al. | 606/139 |
| 2003/0144656 A1 | 7/2003 | Ocel et al. | |
| 2003/0158547 A1 | 8/2003 | Phan | |
| 2003/0158548 A1 | 8/2003 | Phan et al. | |
| 2003/0158549 A1 | 8/2003 | Swanson | |
| 2004/0059324 A1 | 3/2004 | Francischelli et al. | |
| 2004/0147943 A1 * | 7/2004 | Kobayashi | 606/158 |
| 2004/0186467 A1 | 9/2004 | Swanson et al. | |
| 2005/0019545 A1 | 1/2005 | Riebel | |
| 2005/0019653 A1 | 1/2005 | Dahlberg | |
| 2005/0049618 A1 * | 3/2005 | Masuda et al. | 606/151 |
| 2005/0119648 A1 | 6/2005 | Swanson | |
| 2005/0119654 A1 | 6/2005 | Swanson et al. | |
| 2005/0215993 A1 | 9/2005 | Phan | |
| 2005/0277959 A1 * | 12/2005 | Cosgrove et al. | 606/151 |
| 2006/0063973 A1 * | 3/2006 | Makower et al. | 600/114 |
| 2006/0155272 A1 | 7/2006 | Swanson | |
| 2006/0195080 A1 | 8/2006 | Ebert | |

FOREIGN PATENT DOCUMENTS

| | | |
|---|---|---|
| EP | 11255499 A2 | 8/2001 |
| EP | 1476089 B1 | 8/2005 |
| JP | 2001515751 | 9/2001 |
| JP | 2001522622 | 11/2001 |
| WO | WO 99/12488 A1 | 3/1999 |
| WO | WO 99/23933 A2 | 5/1999 |
| WO | WO 00/24330 A1 | 5/2000 |
| WO | WO 03/070114 A1 | 8/2003 |

OTHER PUBLICATIONS

Amendment dated Jul. 14, 2003, for U.S. Appl. No. 10/080,374, filed Feb. 19, 2002, Inventor: David K. Swanson (17 pages).

Office Action dated Oct. 9, 2003, for U.S. Appl. No. 10/080,374, filed Feb. 19, 2002, Inventor: David K. Swanson (12 pages).

Amendment dated Jan. 15, 2004, for U.S. Appl. No. 10/080,374, filed Feb. 19, 2002, Inventor: David K. Swanson (13 pages).

Advisory Action dated Feb. 3, 2004, for U.S. Appl. No. 10/080,374, filed Feb. 19, 2002, Inventor: David K. Swanson (2 pages).

Request for Continued Examination dated Feb. 5, 2004, for U.S. Appl. No. 10/080,374, filed Feb. 19, 2002, Inventor: David K. Swanson (2 pages).

Office Action dated Mar. 24, 2004, for U.S. Appl. No. 10/080,374, filed Feb. 19, 2002, Inventor: David K. Swanson (10 pages).

Amendment dated May 24, 2004, for U.S. Appl. No. 10/080,374, filed Feb. 19, 2002, Inventor: David K. Swanson (18 pages).

Office Action dated Sep. 30, 2004, for U.S. Appl. No. 10/080,374, filed Feb. 19, 2002, Inventor: David K. Swanson (9 pages).

Amendment dated Dec. 7, 2004, for U.S. Appl. No. 10/080,374, filed Feb. 19, 2002, Inventor: David K. Swanson (15 pages).

Advisory Action dated Jan. 3, 2005, for U.S. Appl. No. 10/080,374, filed Feb. 19, 2002, Inventor: David K. Swanson (2 pages).

Request for Continued Examination dated Jan. 7, 2005, for U.S. Appl. No. 10/080,374, filed Feb. 19, 2002, Inventor: David K. Swanson (2 pages).

Interview Summary dated Feb. 14, 2005, for U.S. Appl. No. 10/080,374, filed Feb. 19, 2002, Inventor: David K. Swanson (2 pages).

Office Action dated Feb. 14, 2005, for U.S. Appl. No. 10/080,374, filed Feb. 19, 2002, Inventor: David K. Swanson (5 pages).

(56) References Cited

OTHER PUBLICATIONS

Amendment dated Mar. 8, 2005, for U.S. Appl. No. 10/080,374, filed Feb. 19, 2002, Inventor: David K. Swanson (8 pages).
Notice of Non-Compliant Amendment dated Mar. 9, 2005, for U.S. Appl. No. 10/080,374, filed Feb. 19, 2002, Inventor: David K. Swanson (2 pages).
Response dated Apr. 2, 2005, for U.S. Appl. No. 10/080,374, filed Feb. 19, 2002, Inventor: David K. Swanson (6 pages).
Office Action dated May 18, 2005, for U.S. Appl. No. 10/080,374, filed Feb. 19, 2002, Inventor: David K. Swanson (8 pages).
Amendment dated Oct. 17, 2005, for U.S. Appl. No. 10/080,374, filed Feb. 19, 2002, Inventor David K. Swanson (15 pages).
Office Action dated Jan. 9, 2006, for U.S. Appl. No. 10/080,374, filed Feb. 19, 2002, Inventor David K. Swanson (10 pages).
Amendment dated Apr. 12, 2006, for U.S. Appl. No. 10/080,374, filed Feb. 19, 2002, Inventor: David K. Swanson (17 pages).
Advisory Action dated Apr. 24, 2006, for U.S. Appl. No. 10/080,374, filed Feb. 19, 2002, Inventor: David K. Swanson (3 pages).
Office Action dated Jun. 14, 2006, for U.S. Appl. No. 10/080,374, filed Feb. 19, 2002, Inventor: David K. Swanson (8 pages).
Amendment dated Oct. 28, 2006, for U.S. Appl. No. 10/080,374, filed Feb. 19, 2002, Inventor: David K. Swanson (11 pages).
Office Action dated Jan. 9, 2007, for U.S. Appl. No. 10/080,374, filed Feb. 19, 2002, Inventor: David K. Swanson (9 pages).
Amendment dated Mar. 9, 2007, for U.S. Appl. No. 10/080,374, filed Feb. 19, 2002, Inventor: David K. Swanson (10 pages).
Advisory Action dated Mar. 21, 2007, for U.S. Appl. No. 10/080,374, filed Feb. 19, 2002, Inventor: David K. Swanson (3 pages).
Request for Continued Examination and Amendment dated Apr. 9, 2007, for U.S. Appl. No. 10/080,374, filed Feb. 19, 2002, Inventor: David K. Swanson (11 pages).
Office Action dated Apr. 19, 2007, for U.S. Appl. No. 10/080,374, filed Feb. 19, 2002, Inventor: David K. Swanson (12 pages).
Amendment dated Jul. 19, 2007, for U.S. Appl. No. 10/080,374, filed Feb. 19, 2002, Inventor: David K. Swanson (12 pages).
Office Action dated Oct. 9, 2007, for U.S. Appl. No. 10/080,374, filed Feb. 19, 2002, Inventor: David K. Swanson (15 pages).
Amendment dated Oct. 31, 2007, for U.S. Appl. No. 10/080,374, filed Feb. 19, 2002, Inventor: David K. Swanson (23 pages).
Office Action dated Jan. 9, 2008, for U.S. Appl. No. 10/080,374, filed Feb. 19, 2002, Inventor: David K. Swanson (6 pages).
Response dated Feb. 6, 2008, for U.S. Appl. No. 10/080,374, filed Feb. 19, 2002, Inventor: David K. Swanson (6 pages).
PCT International Preliminary Examination Report for PCT/US2002/038924, Applicant: Scimed Life Systems, Inc., Form PCT/IPEA/409, dated May 27, 2004 (5 pages).
PCT International Search Report for PCT/US2002/038924, Applicant: Scimed Life Systems, Inc., Forms PCT/ISA/210 and PCT/ISA/220, dated May 6, 2003 (7 pages).
Office Action dated Jan. 30, 2008, for Japanese Patent Application No. 2003-569081, filed Nov. 25, 2002, Applicant: Boston Scientific Limited (5 pages).
Office Action dated Apr. 17, 2008 in U.S. Appl. No. 10/080,374, filed Feb. 19, 2002 (17 pages).
Amendment dated Jun. 26, 2008 in U.S. Appl. No. 10/080,374, filed Feb. 19, 2002 (18 pages).
Office Action dated Sep. 22, 2008 in U.S. Appl. No. 10/080,374, filed Feb. 19, 2002 (16 pages).
Amendment dated Nov. 19, 2008 in U.S. Appl. No. 10/080,374, filed Feb. 19, 2002 (12 pages).
Amendment dated Dec. 22, 2008 in U.S. Appl. No. 10/080,374, filed Feb. 19, 2002 (13 pages).
Office Action dated Nov. 27, 2008 in JP Application Serial No. 2003-569081; filed Nov. 25, 2002, Applicant: Boston Scientific Limited (4 pages).
Papers from file history for related U.S. Appl. No. 10/080,374, filed Feb. 19, 2002, Applicant Boston Scientific, including: Amendment response to Office Action dated Mar. 11, 2009, for U.S. Appl. No. 10/080,374, response submitted on Jun. 3, 2009. (8 pages).
Office Action dated Mar. 11, 2009 for U.S. Appl. No. 10/080,374, filed Feb. 19, 2002, inventor David K. Swanson, (13 pages).

* cited by examiner

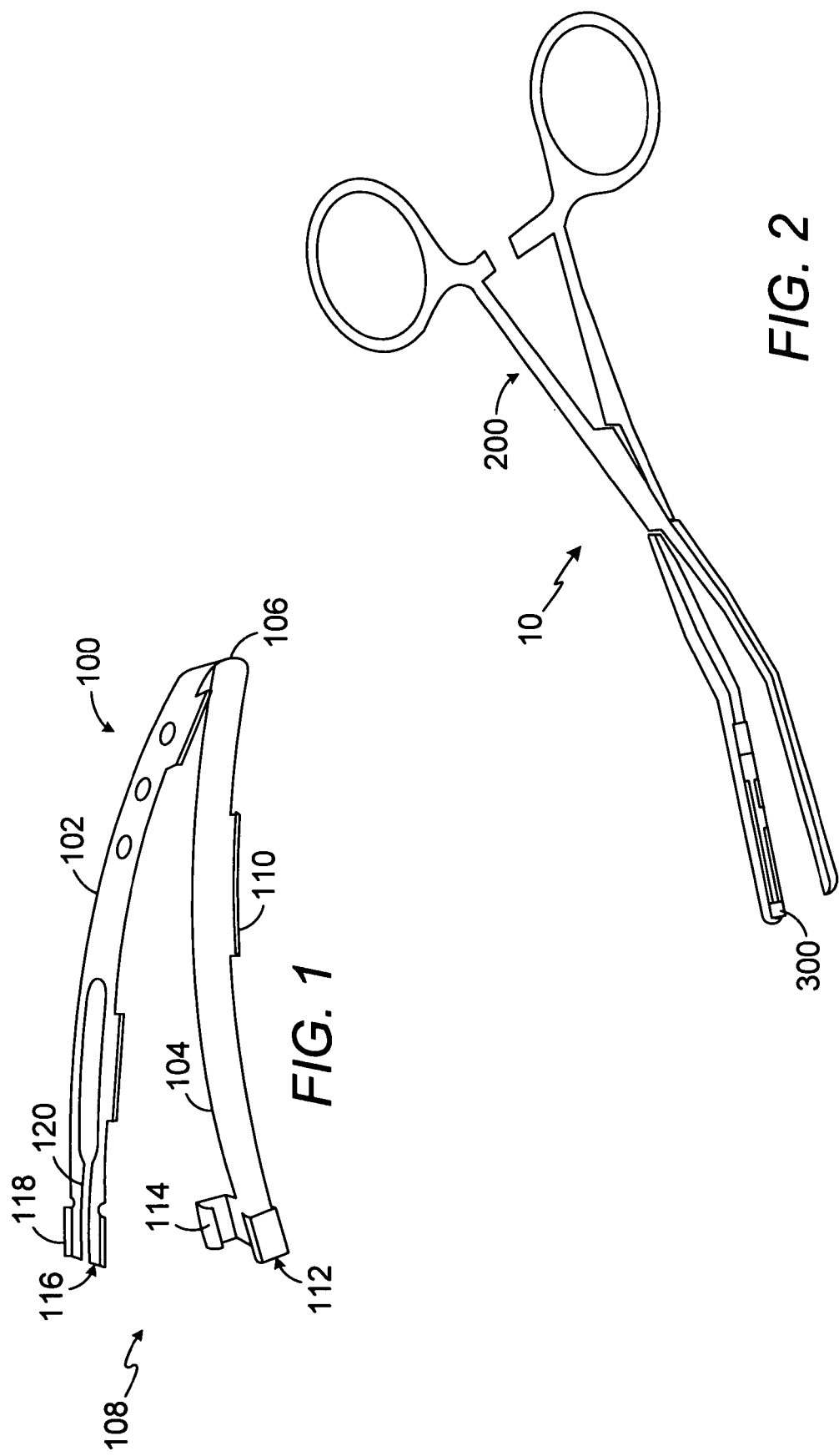

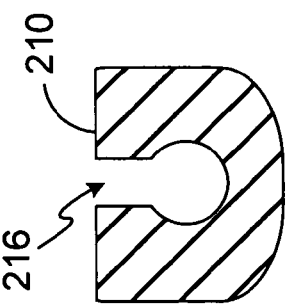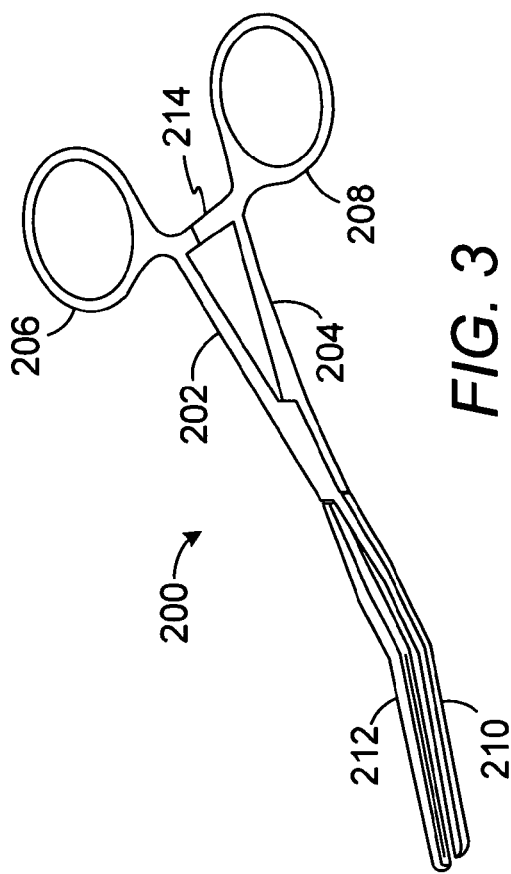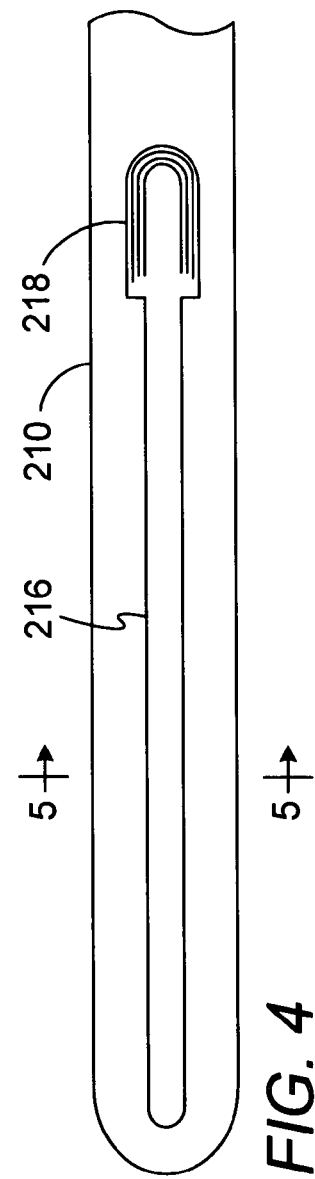

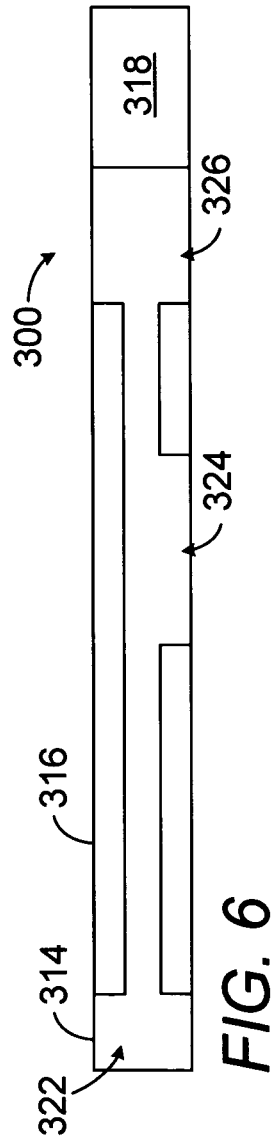
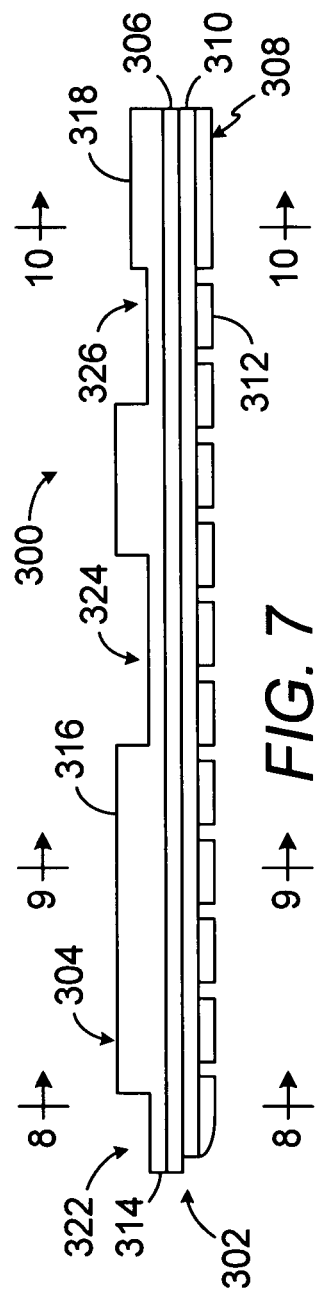
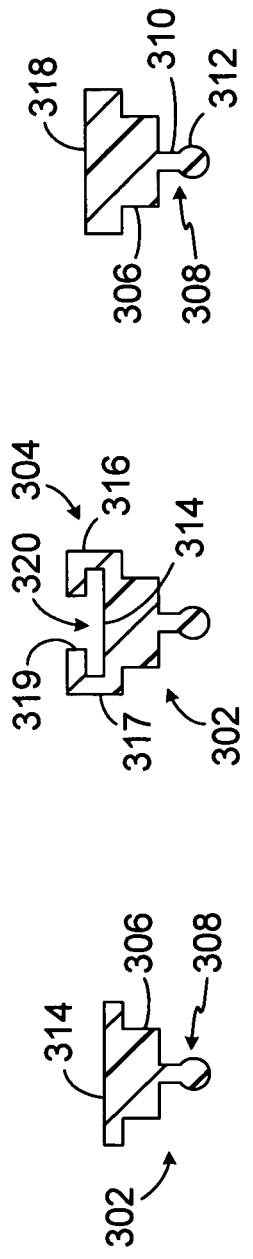
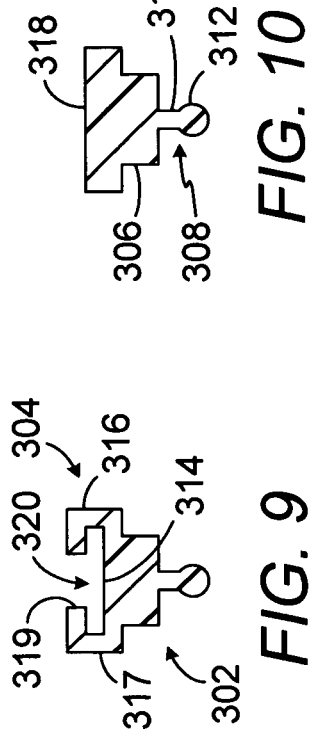
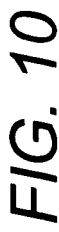
FIG. 6
FIG. 7
FIG. 8
FIG. 9
FIG. 10

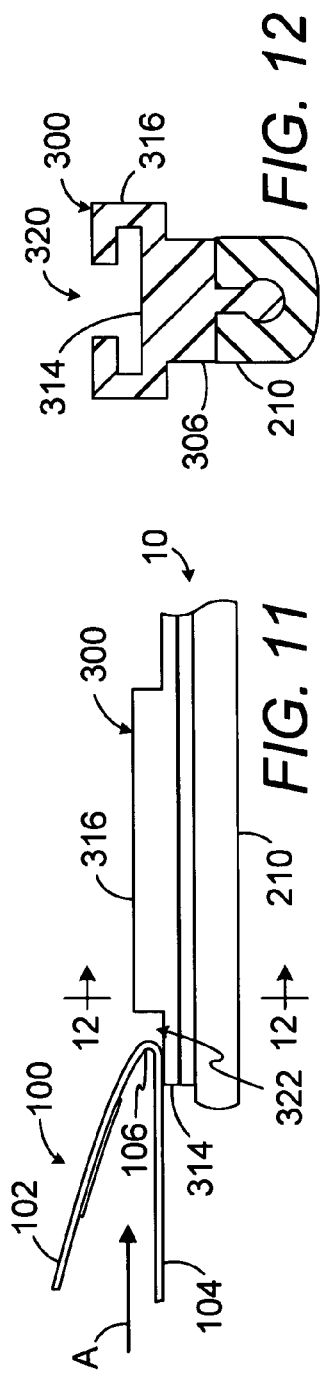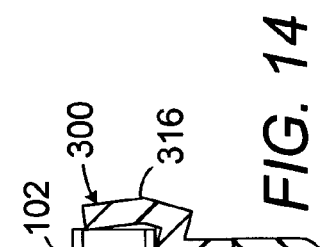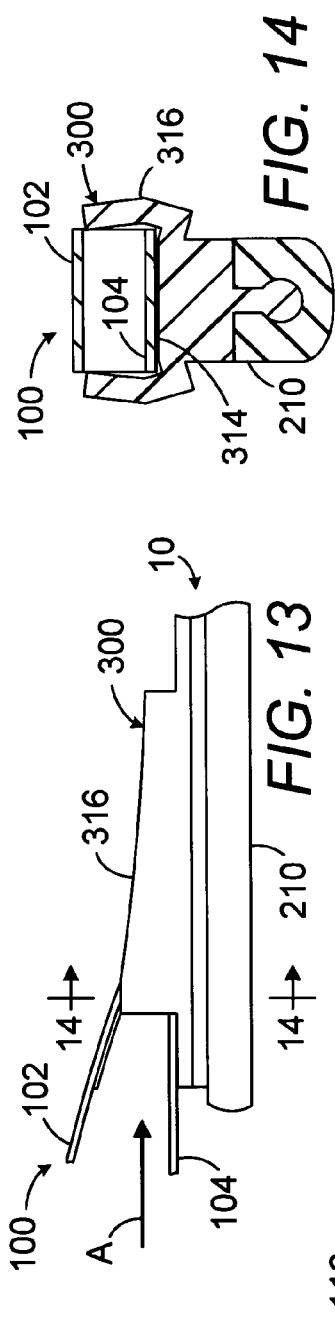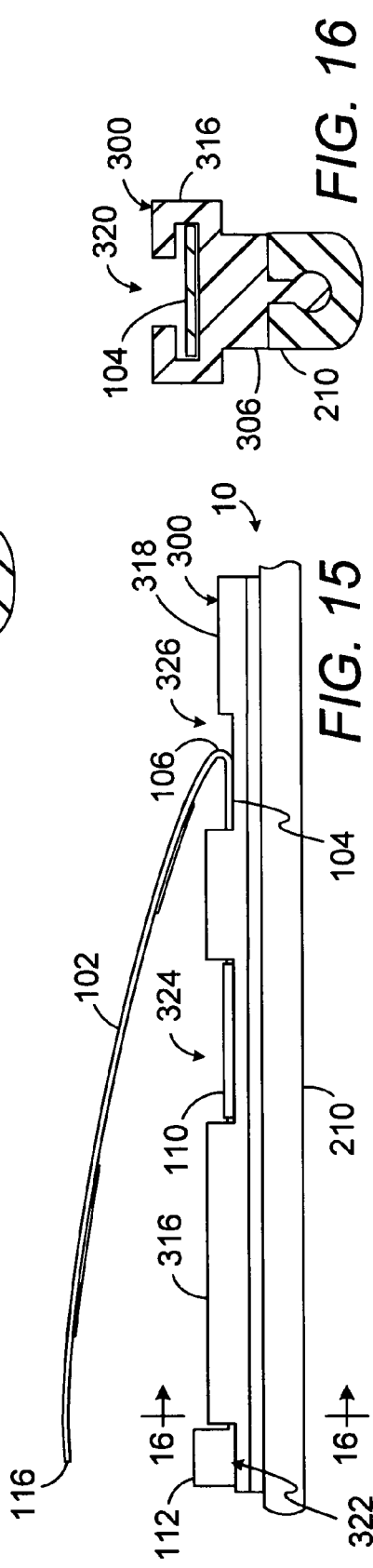

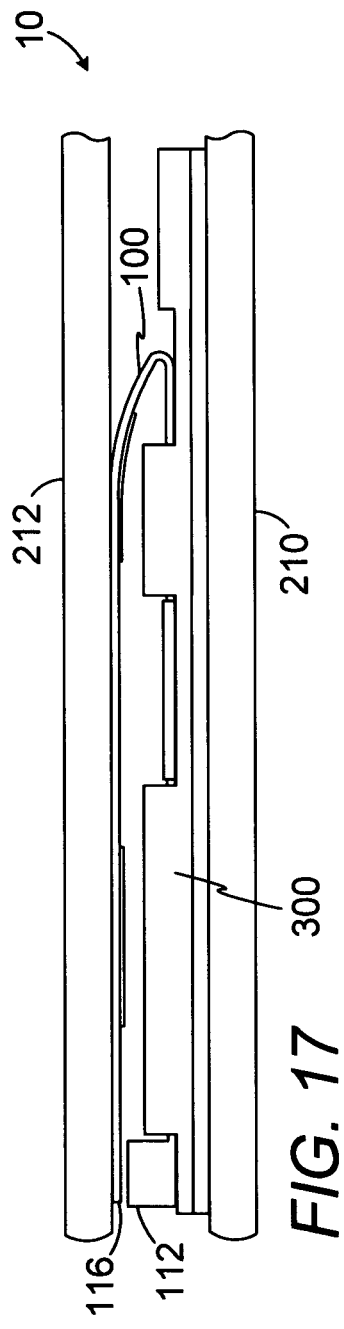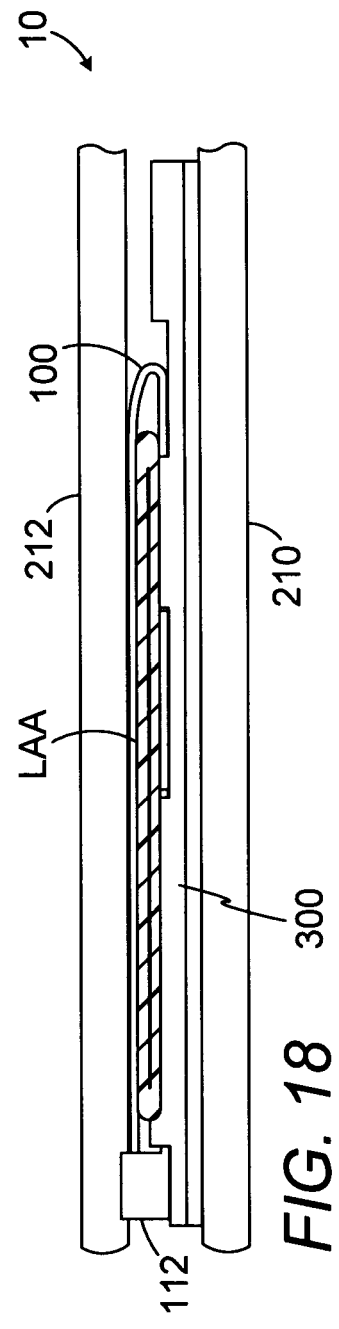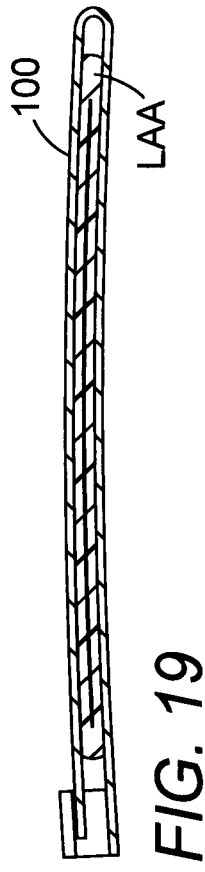
FIG. 17
FIG. 18
FIG. 19

SURGICAL CLIP APPLICATOR AND APPARATUS INCLUDING THE SAME

BACKGROUND OF THE INVENTIONS

1. Field of Inventions

The present inventions relate generally to devices for delivering and installing surgical clips.

2. Description of the Related Art

There are many instances where surgical clips are secured to tissue within a patient. One example of such a procedure is the treatment of atrial fibrillation. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. The wavelets (called "reentry circuits") disrupt the normally uniform activation of the left and right atria. Because of a loss of atrioventricular synchrony, the people who suffer from atrial fibrillation also suffer the consequences of impaired hemodynamics and loss of cardiac efficiency. They are also at much greater risk of strokes and other thromboembolic complications because of loss of effective contraction and atrial stasis. With respect to strokes, thrombus can form in left atrial appendage, break off, and cause a stroke. The risk of stroke for people with atrial fibrillation is about five (5) times that of those who do not have atrial fibrillation.

Electrosurgical devices have been used in minimally invasive procedures to form a set of three transmural epicardial encircling lesions that cures paroxysmal atrial fibrillation in most patients. The epicardial lesion set that typically cures paroxysmal atrial fibrillation includes an encircling lesion around the right pulmonary vein pair, an encircling lesion around the left pulmonary vein pair and an encircling lesion around the left atrial appendage. Additional epicardial lesions are frequently required for patients with persistent or permanent atrial fibrillation. A transmural "connecting" lesion that connects the lesion around the right pulmonary vein pair to the lesion around the left pulmonary vein pair may be required if these lesions do not overlap, and a transmural connecting lesion that connects the lesion around the left pulmonary vein pair to the lesion around the left atrial appendage may be required if these lesions do not overlap. Electrosurgical clamps may be used to form the epicardial encircling lesions and electrosurgical probes may be used to form the epicardial connecting lesions. Exemplary electrosurgical clamps and surgical probes are disclosed in U.S. Pat. Nos. 6,142,994 6,610,055 and U.S. Patent Pub. Nos. 2003/ 0158547 A1 and 2005/0119654 A1. In minimally invasive procedures, access to the heart is typically obtained via a thoracotomy and a relatively small (e.g. about 10 mm in diameter) access port.

There is, unfortunately, some likelihood that a patient's atrial fibrillation will not be cured by the above-described minimally invasive epicardial procedure and such a patient will also continue suffer from the associated increase in the risk of stroke. In context of more invasive atrial fibrillation treatments, such as open heart surgical maze procedures, one method of reducing subsequent stroke risk in patients is to isolate the interior of the atrial appendage from the left atria. This eliminates the possibility of thrombus within the atrial appendage entering the blood stream. The isolation may be accomplished by suturing the base of the atrial appendage closed, or by applying a clip by hand to epicardial surface at the base of the atrial appendage.

The present inventor has determined that although the use of a clip is a convenient way to isolate an atrial appendage, a need exist for a device that is capable of delivering a clip to a target tissue structure during minimally invasive surgical procedures, where application by hand is not possible.

SUMMARY OF SOME OF THE INVENTIONS

An apparatus in accordance with an invention herein includes a mounting portion configured to be removably secured to a clamp and an engagement portion configured to releasably engage at least a portion of a surgical clip. Another apparatus in accordance with an invention herein includes a clamp and a clip applicator, associated with the clamp, including an engagement portion configured to releasably engage at least a portion of a surgical clip. Still another apparatus in accordance with an invention herein is a unitary structure configured to be removably secured to a clamp and to releasably engage at least a portion of a surgical clip.

Such apparatus provide a number of advantages. For example, the present apparatus may be used to deliver a surgical clip to a target tissue structure during minimally invasive surgical procedures. More specifically, after a surgical clip is removably secured to a clamp, the clamp may be moved to a closed (or substantially closed) orientation so that the clip and clamp can be inserted into a patient through a relatively small access port. The clamp may then be used to positing the surgical clip on the target tissue structure. Once the surgical clip is in place, the clamp may be separated from the clip and removed from the patient.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of embodiments of the inventions will be made with reference to the accompanying drawings.

FIG. 1 is a perspective view of one example of a conventional clip that may be used in combination with a present invention.

FIG. 2 is a perspective view of a clip application apparatus in accordance with one embodiment of a present invention.

FIG. 3 is a perspective view of a clamp.

FIG. 4 is a plan view of a portion of the clamp illustrated in FIG. 3.

FIG. 5 is a section view taken along line 5-5 in FIG. 4.

FIG. 6 is a plan view of a portion of a clip applicator in accordance with one embodiment of a present invention.

FIG. 7 is a side view of the clip applicator illustrated in FIG. 6.

FIG. 8 is a section view taken along line 8-8 in FIG. 7.

FIG. 9 is a section view taken along line 9-9 in FIG. 7.

FIG. 10 is a section view taken along line 10-10 in FIG. 7.

FIG. 11 is a side view showing a clip prior to being secured to a clip application apparatus in accordance with one embodiment of a present invention.

FIG. 12 is a section view taken along line 12-12 in FIG. 11.

FIG. 13 is a side view showing the clip being secured to the clip application apparatus in illustrated in FIG. 11.

FIG. 14 is a section view taken along line 14-14 in FIG. 13.

FIG. 15 is a side view showing the clip secured to the clip application apparatus in illustrated in FIG. 10.

FIG. 16 is a section view taken along line 16-16 in FIG. 15.

FIG. 17 is a side view showing the clip application apparatus illustrated in FIG. 11 compressing the clip.

FIG. 18 is a side, section view showing the clip application apparatus illustrated in FIG. 11 locking the clip on a tissue structure.

FIG. 19 is a section view showing the clip on a tissue structure after the clip application apparatus has been withdrawn.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

Although the present inventions are not limited to use with any particular surgical clips, one example of a conventional surgical clip that may be inserted into a patient and secured to a tissue structure is illustrated in FIG. 1. The exemplary surgical clip 100 is a unitary structure that includes a top portion 102 and a bottom portion 104 that pivot relative to one another about a pre-bent hinge 106 that is biased to the open orientation illustrated in FIG. 1. The surgical clip 100 also includes a locking apparatus 108 and a plurality of tissue engagement devices 110. Once the surgical clip 100 is locked in place, the tissue engagement devices 110 will prevent the surgical clip from moving by pressing into the tissue. Scar tissue will also form around the tissue engagement devices 110, which further prevents movement. In the illustrated embodiment, the locking apparatus 108 includes a first locking member 112 with a pair of inwardly extending cam surfaces 114 and a second locking member 116 with a pair of deflectable latches 118. A cutout 120 in the top portion 102 of the surgical clip 100 allows the latches 118 to move relative to one another.

The exemplary surgical clip 100 illustrated in FIG. 1 may be secured to a tissue structure, either by hand during invasive surgical procedures or through the use the present surgical clip application apparatus 10 illustrated in FIG. 2 during minimally invasive procedures, as follows. After the surgical clip 100 is positioned about the target tissue structure, force is applied to the top and bottom portions 102 and 104 and, as the top and bottom portions approach the locked orientation (FIG. 19), the latches 118 engage the cam surfaces 114 and move toward one another. The latches 118 continue to move toward one another until they pass the cam surfaces 114, at which time they spring apart. The surgical clip 100 is then released and the biasing force of the hinge 106 forces the now spread apart latches 118 against the underside of the cam surfaces 114, thereby preventing the surgical clip 100 from returning to the open position. The surgical clip 100 may also be unlocked, if necessary, by pushing the latches 118 toward one another so that the biasing force of the hinge 106 can force the latches 118 through the cam surfaces 116.

The exemplary surgical clip application apparatus 10 illustrated in FIG. 2 includes a clamp 200 and a surgical clip applicator 300 carried by the clamp. As used herein, the term "clamp" includes, but is not limited to, clamps, forceps, hemostats, and any other surgical device that includes a pair of opposable clamp members, at least one of which is movable relative to the other. In some instances, the clamp members are connected to a scissors-like arrangement including a pair of handle supporting arms that are pivotably connected to one another. The clamp members are secured to one end of the arms and the handles are secured to the other end. Certain clamps that are particularly useful in minimally invasive procedures also include a pair of handles and a pair of clamp members. Here, however, the clamp members and handles are not mounted on the opposite ends of the same arm. Instead, the handles are carried by one end of an elongate housing and the clamp members are carried by the other. A suitable mechanical linkage located within the housing causes the clamp members to move relative to one another in response to movement of the handles. The clamp members may be linear or have a predefined curvature that is optimized for a particular surgical procedure or portion thereof. The clamp members may also be rigid or malleable.

One example of a clamp is generally represented by reference numeral 200 in FIGS. 2-5. Referring more specifically to FIGS. 3-5, the clamp 200 includes a pair of rigid arms 202 and 204 that are pivotably connected to one another by a pin (not shown). The proximal ends of the arms 202 and 204 are respectively connected to a pair handle members 206 and 208, while the distal ends are respectively connected to a pair of clamp members 210 and 212. The clamp members 210 and 212 may be rigid or malleable and, if rigid, may be linear or have a pre-shaped bend (as shown). A locking device 214 locks the clamp in the closed orientation, and prevents the clamp members 210 and 212 from coming any closer to one another than is illustrated in FIG. 3. The clamp 200 is also configured for use with a pair of soft, deformable inserts (not shown) that may be removably carried by the clamp members 210 and 212 and allow the clamp to firmly grip a bodily structure without damaging the structure. To that end, the clamp members 210 and 212 each include a slot 216 (FIGS. 4 and 5) that is provided with a sloped inlet area 218 and the inserts include mating structures that are removably friction fit within the slots. The present surgical clip applicators may be mounted on one of the clamp members in place of the insert and, typically, there will be no insert on the other clamp member.

Turning to FIGS. 6-10, the exemplary surgical clip applicator 300 includes a mounting portion 302, which secures the surgical clip applicator to the clamp 200, and an engagement portion 304, which releasably engages the surgical clip 100. The mounting portion 302 includes a base member 306 and a connector 308 that is configured to removably mate with the clamp slot 216 (FIGS. 4 and 5). The exemplary connector 308 has a relatively thin portion 310 and a relatively wide portion 312, which may consist of a plurality of spaced members (as shown) or an elongate unitary structure, in order to correspond to the shape of the slot 216. The mounting portion may be modified so that surgical clip applicators in accordance with the present inventions may be used in conjunction with clamps that do not include a clamp member slot. Here, the connector 308 may be eliminated and the base member reconfigured such that it includes a longitudinally extending aperture into which a clamp member may be inserted. The aperture and base member should be sized and shaped such that the base member will be forced to stretch when the clamp member is inserted in order to create a tight interference fit between the base member and clamp member.

The engagement portion 304 includes a bottom surface 314, flexible flaps 316 and an end stop 318. The exemplary flaps 316, which extend longitudinally, have an inverted L-shape and together define a slot 320, are positioned along the sides of the bottom surface 314 and are used to releasably engage the surgical clip. The flaps 316 have a fixed end 317 (FIG. 9), which is connected to the bottom surface 314, and a free end 319. Although the present inventions are not limited to use with any particular surgical clip, the exemplary surgical clip applicator 300 is configured for use with the surgical clip 100 illustrated in FIG. 1. To that end, the distal end of the surgical clip applicator 300 includes an open region 322 (i.e. a region without one or more of the flexible flaps 316) for the first locking member 112, an open region 324 for the tissue engagement device 110 on the clip bottom portion 104, and an open region 326 for the hinge 106.

One method of securing the exemplary surgical clip 100 to the exemplary surgical clip applicator 300 on the surgical clip application apparatus 10 is illustrated in FIGS. 11-16. Referring first to FIGS. 11 and 12, the surgical clip 100 is placed on the engagement portion bottom surface 314 at the open region 324 while the surgical clip applicator 300 is in a relaxed state. The surgical clip 100, which is oriented such that the hinge 106 faces proximally, is then moved in the direction indicated by arrow A (i.e. along the longitudinal axis of the surgical clip applicator 300). The surgical clip 100 causes the flexible clip applicator flaps 316 to deflect in the manner illustrated in FIGS. 13 and 14 as the surgical clip moves through the slot 320 in the direction indicated by arrow A. More specifically, the portions of the flaps 316 that are adjacent to the clip hinge 106 will deflect when aligned with the clip hinge and will return to the unstressed state after the clip hinge moves past them. The movement in the direction indicated by arrow A, and corresponding deflection of the portions of the flaps 316 that are adjacent to the clip hinge 106, will continue until the surgical clip 100 reaches the stored position illustrated in FIGS. 15 and 16. The end stop 318 may, if necessary, be used to prevent the surgical clip 100 from moving too far in the proximal direction. In the stored position, the clip bottom portion 104 is held within the slot 320, the first locking member 112 is aligned with the open region 322, the tissue engagement device 110 on the clip bottom portion 104 is aligned with the open region 324, and the hinge 106 is aligned with the open region 326. The surgical clip 100 is, at this point, "releasably engaged" to the clamp member 210, i.e. the surgical clip is secured to the clamp member 210 in such a manner that the surgical clip will remain secured to the clamp member 210 without assistance from (and in the absence of contact with) the clamp member 212, yet can also be readily disengaged from the clamp member 210.

It should be noted that the exemplary surgical clip application apparatus 10 includes a single surgical clip applicator 300. As such, the clip top portion 102 is not directly secured to the surgical clip application apparatus 10. There may, however, be some instances where a pair of surgical clip applicators 300 are used to secure a surgical clip to both of the clamp members 210 and 212 in the surgical clip application apparatus 10.

Once the surgical clip 100 is in the stored position, and is removably secured to the surgical clip applicator 300, as well as to the clamp 200 by way of the surgical clip applicator, the surgical clip may be inserted into the patient with the surgical clip application apparatus 10. As illustrated for example in FIG. 17, the clamp members 210 and 212 may be brought into close proximity to one another, although not so close that they cause the clip locking members 112 and 116 on the surgical clip 100 to engage one another, so that the distal portion of the surgical clip application apparatus 10 can be inserted with the surgical clip into a patient by way of a thoracotomy and/or a relatively small access port (e.g. about 10 mm). Once inside the patient, the clamp members 210 and 212 may be moved apart so that the surgical clip 100 will return to its open state (or partially opened state) and be positioned around the target tissue structure, e.g. around the epicardial base of the left atrial appendage LAA. Next, as illustrated in FIG. 18, the clamp members 210 and 212 may be used to compress the surgical clip 100 around the base of left atrial appendage LAA until the locking members 112 and 116 lock the surgical clip in place. The surgical clip application apparatus 10 may then be opened and moved proximally, while the surgical clip 100 remains secured to the left atrial appendage LAA, which cause the flexible clip applicator flaps 316 to deflect and release the surgical clip.

With respect to materials and dimensions, and although the present surgical clip applicators are not limited to any particular materials and dimensions, surgical clip applicators in accordance with the present inventions may be formed from any suitable flexible biocompatible material. Exemplary materials include polyurethane silicone, polyurethane/silicone blends and Pebax blends with a Shore hardness of about 30D to 55D. Preferably, the flaps 316 will be extremely flexible, i.e. just rigid enough to prevent the surgical clip 100 from falling off of the surgical clip applicator 300, in order to facilitate separation of the surgical clip and surgical clip application apparatus 10 after the surgical clip has been locked onto the target tissue structure. The size of the surgical clip applicator 300 will, of course depend upon the size of the surgical clip that it is intended to hold. In the illustrated embodiment, the surgical clip applicator is about 40 mm to 55 mm long and about 7 mm to 10 mm wide at its widest point. The flaps 316 are about 1 mm to 3 mm high (measured from the bottom surface 314) and extend inwardly from the outer edge about 0.5 mm to 1.5 mm. The slot 320 is about 6 mm to 7 mm wide and about 0.5 mm to 1.5 mm high (measured from the bottom surface 314 to the underside of the flap 316) at its widest point, and about 4 mm to 5 mm wide and about 2 mm to 3 mm high (measured from the bottom surface 314 to the top of the flap 316) at its narrowest point.

Turning to manufacture, and although the present surgical clip applicators are not limited to any particular manufacturing processes, surgical clip applicators in accordance with the present inventions may be formed as unitary structures (i.e. one piece structures) with a molding process such as injection molding or casting. Alternatively, the surgical clip applicators may be formed from multiple parts that are individually molded or machined and then secured to one another.

In other exemplary surgical clip application apparatus, the clamp and surgical clip applicator described above may be combined into an integral unit that cannot be readily separated. For example, the surgical clip applicator may be molded onto a clamp member. Such a surgical clip applicator would, for example, extend completely around the clamp member and/or include portions that are molded into the clamp member slots.

Although the inventions disclosed herein have been described in terms of the preferred embodiments above, numerous modifications and/or additions to the above-described preferred embodiments would be readily apparent to one skilled in the art. By way of example, but not limitation, the flexible flaps may, instead of being L-shaped, be curved or planar. Planar flexible flap would be oriented at an acute angle with respect to the bottom surface 314. Single flap configurations are also possible. It is intended that the scope of the present inventions extend to all such modifications and/or additions and that the scope of the present inventions is limited solely by the claims set forth below.

I claim:

1. An apparatus for isolating an atrial appendage of a patient, the apparatus comprising:
a surgical clip that locks onto the atrial appendage of the patient, the surgical clip including a top portion and a bottom portion; and
a surgical clip applicator that releasably engages the surgical clip, the surgical clip applicator including bottom surface extending between a first flexible flap and a second flexible flap, the first flexible flap having a fixed end connected to the bottom surface and a free end, the second flexible flap having a fixed end connected to the bottom surface and a free end, and the bottom surface comprising a flat surface extending the width of the clip and from the fixed end of the first flap to the fixed end of the second flap, wherein the first and second flexible flaps are sufficiently rigid to prevent the surgical clip from falling off of the surgical clip applicator when the bottom portion of the surgical clip is engaged to the surgical applicator between the first and second flexible flaps and the surgical clip applicator is in a relaxed state, wherein the free end of the first flexible flap extends between the top and bottom portions of the surgical clip when the surgical clip is engaged to the surgical clip applicator, wherein the free end of the second flexible flaps extends between the top and bottom portions of the surgical clip when the surgical clip is engaged to the surgical clip applicator, and wherein the first and second flexible flaps are flexible and configured to deflect to release the surgical clip from the surgical clip applicator when the surgical clip is locked onto the atrial appendage.

2. The apparatus of claim 1, wherein the first and second flexible flaps deflect during engagement of the surgical clip to the surgical clip applicator.

3. The apparatus of claim 1, wherein the first and second flexible flaps comprise a flexible biocompatible material.

4. The apparatus of claim 1, wherein the first and second flexible flaps comprise a polyurethane silicone material.

5. The apparatus of claim 1, wherein the first and second flexible flaps comprise a polyurethane/silicone blend material.

6. The apparatus of claim 1, wherein the first and second flexible flaps comprise a Pebax blend material.

7. The apparatus of claim 1, wherein the first and second flexible flaps comprise a material having a Shore hardness within a range from about 30D to 55D.

8. The apparatus of claim 1, wherein the bottom surface of the surgical clip applicator together with the first and second flexible flaps defines a slot that receives the bottom portion of the surgical clip.

9. The apparatus of claim 1, wherein a central section of the clip bottom portion contacts the bottom surface of the applicator when the surgical clip is engaged to the surgical clip applicator.

10. The apparatus of claim 1, wherein the apparatus provides a continuous interface between the bottom surface of the applicator and the bottom portion of the clip, the continuous interface extending between the fixed ends of the first and second flexible flaps, when the surgical clip is engaged to the surgical clip applicator.

11. The apparatus of claim 1, wherein the first and second flexible flaps assume a closed position in the absence of any external force, the closed position preventing the surgical clip from falling off of the surgical clip applicator when the bottom portion of the surgical clip is engaged to the surgical applicator between the first and second flexible flaps.

* * * * *